United States Patent [19]

Vodian et al.

[11] Patent Number: 4,703,001

[45] Date of Patent: Oct. 27, 1987

[54] IMMUNOASSAY FOR THE DETECTION OF SERUM ANALYTES USING PH DEPENDENT CHASTROPIC ACIDS

[75] Inventors: Morton A. Vodian, Escondido; Eric S. Bean, San Diego, both of Calif.

[73] Assignee: Synbiotics, Corporation, San Diego, Calif.

[21] Appl. No.: 790,469

[22] Filed: Oct. 23, 1985

[51] Int. Cl.$^4$ .................. C12Q 1/70; G01N 33/53; G01N 33/564

[52] U.S. Cl. .......................... 435/5; 435/4; 435/7; 435/810; 436/506; 436/518; 436/528; 436/808; 436/809; 436/811; 436/825; 436/826

[58] Field of Search ............... 436/506, 518, 528, 808, 436/809, 811, 825, 826; 435/4, 5, 7, 810

[56] References Cited

U.S. PATENT DOCUMENTS

| | | | |
|---|---|---|---|
| 4,322,495 | 3/1982 | Kato | 435/7 |
| 4,536,478 | 8/1985 | Sokoloff et al. | 436/825 |
| 4,551,426 | 11/1985 | Freytag et al. | 436/541 |

FOREIGN PATENT DOCUMENTS

| | | | |
|---|---|---|---|
| 38181 | 10/1981 | European Pat. Off. | 436/518 |
| 148166 | 7/1985 | European Pat. Off. | 435/7 |

OTHER PUBLICATIONS

Boto et al., J. Immunol., vol. 133(2) 981-7 1984.
Eskola et al., Clin. Chem. 31(10) 1985 1731-4.
Vader et al., Clin. Chem. Acta., 80 (1977) 361-72.
Stone et al., J. Immunol. Methods, 31 (1979) 379-87.
Sawyer et al., J. Biological Chem. 248 (1973) 8429-33.
von Schenck et al., Scano. J. Clin. Lab. Invest. 43(1983), 527-31.

*Primary Examiner*—Christine M. Nucker
*Attorney, Agent, or Firm*—Donald G. Lewis

[57] ABSTRACT

The performance of immunoassays for the analysis of serum analytes can be significantly improved by the pretreatment of the sample. Analyte in serum samples is often complexed with serum antibody. Such analyte-antibody complexes can mask the analyte and interfere with analyte specific binding steps of many immunoassays. The serum pretreatment method employs pH dependent chaotropes to dissociate the analyte-antibody complexes in the serum. At low pH, the complexes become dissociated and the antibody becomes denatured. After the dissociation and denaturation of the serum antibody, the serum sample and the chaotrope, contained therein, are then neutralized. Since the serum antibody has been denatured, it does not re-associate with the analyte upon neutralization. After the neutralization step, serum sample can then be analyzed by an immunoassay, without interference from serum antibody. A serum pretreatment kit is essential to the employment of the serum pretreatment method.

15 Claims, No Drawings

IMMUNOASSAY FOR THE DETECTION OF SERUM ANALYTES USING PH DEPENDENT CHASTROPIC ACIDS

BACKGROUND

The invention is an adjunct for enhancing the performance of immunoassays for detecting the presence of analyte in serum. The invention relates to methods and kits for pretreating serum so as to dissociate the analyte from the serum antibody in preparation for an immunoassay analysis of the analyte. More particularly, the invention relates to the use of chaotropic acids for dissociating analyte from serum antibody.

Immunoassays are often employed for detecting the presence of analyte. An example of one such immunoassay is disclosed by David et al. U.S. Pat. No. 4,376,110), commonly known as a "sandwich" immunoassay. According to David's immunoassay, analyte is first exposed to and bound to an immobilized antibody having a specificity for the analyte; the presence of such bound analyte is then determined by a second binding by a labeled soluable antibody, also having a specificity for the analyte. The labeled soluable antibody is conjugated to a label which is easily detected. The label is often an enzyme. After the unbound component of the labeled antibody is washed away, the labeled antibody which remains is proportional to the amount of analyte originally exposed to the immobilized antibody. The immunoassay is called a "sandwich" immunoassay because the analyte is sandwiched between two antibodies, viz. the immobilized antibody and the soluble antibody conjugated to a label.

The immunoassay described by David and similar ELISA procedures may be employed for detecting analyte in serum. However, the performance of such immunoassays will be impaired if the serum sample includes serum antibody having a specificity for the particular analyte. If the analyte is antigenic with respect to the serum donor, the serum sample may include antibody generated by a donor against such analyte. If such serum antibody is not removed from the serum prior to the immunoassay, it will interfere with the performance of commonly employed immunoassays, such as the David immunoassay. The degree of such interference is determined by the donor's antibody titer and the avidity of such serum antibody. In turn, the donor's antibody titer will depend upon the antigenicity of the analyte and the course of the donor's immune response to such analyte.

William F. Feller et al. (European Patent Application Ser. No. 85400002.3: "Brest Cancer Diagnostic Blood Test") disclose adjunct methods for improving the performance of immunoassays for the analysis of serum or plasma analytes. The Feller method employs either chaotropic salts or an aqueous dilution procedure to dissociate the serum of plasma analyte from serum antibody. The dissociated analyte is then dried within the well of a microtiter plate, coating the walls thereof. If chaotropic salts are employed, the residual salts may then be washed from the well. During such wash, the analyte remains attached to the walls of the well and then becomes the object of a subsequent immunoassay procedure.

F. K. de Steenwinkel et al. (European Patent Application Ser. No. 81301559.1: "Agglutination Immunoassays") discloses the addition of chaotropic agents to particle agglutination immunoassays for dissociating analyte from nonspecifically bound serum proteins. Free analyte causes specific agglutination between antibody treated particles. The chaotropic agent remains present throughout the particle agglutination immunoassay. In order to avoid interference with the agglutination process, the concentration of added chaotrope is carefully controlled. If too little chaotrope is present, the nonspecific interference is unabated; if too much chaotrope is present, the specific agglutination is prevented. The de Steenwinkel reference does not disclose that the dissociation and agglutination phases may be separated; the de Steenwinkel reference does not disclose the use of halogenated chaotropic acids.

S. S. Stone et al. (*Journal of Immunological Methods*, vol. 31, pp 379–387 (1979): "Isolation and Purification of Bovine IgM by Dissociating Immunoglobulin-Brucella Complexes") discloses and compares the dissociation of antigen-antibody complexes by the use of water extraction, chaotropic salts (various concentrations of KSCN), and low pH (2M glycine at pH 2.0). The antibody yield for Stone's pH treatment was poor compared to the water extraction and chaotropic salt treatments (9.2% or less). However, subsequent work has shown that the application of denaturing heat (65° C.) with a pH procedure such as Stone's significantly enhances the dissociation process and the resultant yield.

William H. Sawyer (*The Journal of Biological Chemistry*, vol. 248 (24), pp. 8429–8433 (1973): "The Dissociation of Proteins by Chaotropic Salts") discloses and compares the use of chaotropic salts, including the sodium salts of certain halogenated chaotropic acids, buffered between pH 4.6 and pH 7.5, with temperatures between 4° C. and 14° C., to dissociate various proteins. Sawyer found that the effectiveness of the tested chaotropes for dissociating these proteins was partially predicted by the Hofmeister series. Although Sawyer's study included the sodium salts of halogenated chaotropic acids, the study did not determine the effectiveness of halogenated chaotropes as free acids. Between pH 4.6 and pH 7.5, each of the chaotropes studied by Sawyer exist as ionic salts, having lost their dissociable proton.

H. von Schenck et al. (*Scandinavian Journal of Laboratory Investigation*, vol. 43, pp. 527–531 (1983): "Ligand Leakage from Immunoaffinity Column") discloses the use of 1–2M aqueous solutions of formic acid, as a chaotropic agent, for eluting antigen-antibody complexes from immunoaffinity columns. Formic acid is sometimes favored for eluting bound antigen from immunoaffinity columns because, after the elution, the formic acid may then be separated from the eluant by lyophylization. However, von Schenck does not represent that formic acid may be similarly employed for dissociating antigen-antibody complexes within a serum sample; nor does von Schenck disclose the use of halogenated chaotropic acids for dissociating antigen-antibody complexes.

SUMMARY OF THE INVENTION

The invention is a serum pretreatment method employed in conjunction with immunoassays for enhancing the detection of analyte in serum samples. Many analytes are highly antigenic. If the serum donor has produced antibody against the analyte, the formation of antibody complexes with the analyte can interfere with an immunoassay for the detection of serum analyte. The pretreatment method, described herein, dissociates serum antibody and other serum proteins from the analyte in the serum sample. Further, this pretreatment method denatures the dissociated serum antibody and/or other dissociated serum proteins.

The pretreatment method includes a first step for dissociating serum antibody from analyte by the application of chaotropic acids and a second step, performed after the completion of the first step, for neutralizing the chaotropic acid. After completion of the pretreatment method, the serum is ready for analysis by immunoassay, i.e. the analyte is substantially free from its antibody complex and interfering serum antibody and/or other serum proteins are largely denatured. The performance of the subsequent immunoassay is significantly enhanced by the dissociation and denaturation these serum antibodies and/or other serum proteins.

The pretreatment method employs halogenated chaotropic acids which are pH dependent, i.e. the chaotropicity of the chaotrope varies significantly with pH. At acid pH, the chaotropicity is greatly enhanced or activated. At neutral pH, the chaotropicity is greatly reduced or de-activated. During the dissociation step, the pH is low and the chaotropic acid has a high chaotropicity. When the pH is raised during the neutralization step, the chaotropic acid has a reduced chaotropicity. This reduction of chaotropicity allows the subsequent immunoassay to be performed without interference from the continued presence of the chaotrope, viz. the chaotrope will not materially interfere with the binding between serum analyte and the antibody reagents of the immunoassay. The re-association between analyte and the serum antibody is prevented by the fact that the serum antibody is denatured.

Many different immunoassays can achieve an enhanced performance by the employment of the pretreatment method as an adjunct. Radioimmunoassays, immunoassays which employ ELISA procedures, and immunoassays which employ a variety of labels, including fluorophores, chemiluminigenic compounds, latex beads, enzyme cofactors, and enzyme inhibitors, can each achieve an enhanced performance using the pretreatment method. If a pretreatment method employs a chaotropic acid, its utility may be limited to the analysis of acid stable analytes, viz. analytes which are not denatured by exposure to the low pH developed during the dissociation procedure, e.g. a pH of approximately 2.5. Additionally, only those immunoassays which utilize reagents having a tolerance for the low chaotropic form of the chaotrope, i.e. analyte specific antibody of the immunoassay reagent which can bind analyte in the presence of the low chaotropic form of the chaotrope, can achieve an enhanced performance by the employment of the pretreatment method. In other words, the pretreatment method may be usefully employed as an adjunct to an immunoassay only if the immunoassay continues to be operable in the presence of the de-activated chaotrope. Finally, if for some reason, the serum sample is known to contain analyte which is already free and unbound from serum antibody and/or other serum components, then employment of the pretreatment procedure would usually be redundant and would not enhance the performance of the assay.

The pretreatment method is novel because it is the first pretreatment method which recognizes and exploits a chaotrope which has a pH dependent chaotropic effect.

The pretreatment method is novel because it is the first pretreatment method which combines the dissociation and denaturation steps without the application of heat.

DETAILED DESCRIPTION

An aliquot of the serum to be assayed is transferred to a pretreatment well of a microtiter plate and combined with a chaotropic acid. One class of preferred chaotropic acid includes halogenated organic chaotropic acids such as trichloroacetic acid, dichloroacetic acid, chloroacetic acid, trifloroacetic acid, and difloroacetic acid. A second class of preferred chaotropic acids includes perchloric acid. Both classes of chaotropic acid share the common trait that their chaotropicites vary significantly with pH. Each member of these two classes is characterized by an ionic strength, or a range of ionic strengths, within which, at low pH, the member is sufficiently chaotropic to dissociate antibody-antigen complexes, while, upon neutralization, the member's chaotropicity declines sufficiently to allow antibody-antigen complexes to reform. The application of heat is unnecessary to effect this high chaotropicity at low pH.

Both classes of chaotropic acid also share the common trait that the pH range of their highly chaotropic state includes a pH at which serum antibody and/or other serum components which may bind to the analyte (antigen) will denature but acid stable analytes will not. Antibody is denatured by these chaotropic acids at a pH of approximately 2.5. For purposes of this application, analytes are defined as acid stable if they remain native at a pH of 2.5 or less. Typical acid stable analytes include highly glycosylated proteins and peptides. Examples of acid stable analytes include antigens shed from canine heartworm (Dirofilaria immitis) and from feline infectious peritonitis. If an analyte is highly acid stable, i.e. if it maintains a native conformation at a pH significantly below 2.5, a broader range of chaotropic acids may be employed for its dissociation.

The mechanism for chaotropic variability with pH is unknown to the applicant. One possibility is that the protonated and unprotonated forms of these chaotropic acids have markedly different chaotopicities. An other possibility is that the increased presence of hydronium at low pH may change the structure of water so as to initiate new interactions between water and these chaotropic acids. In any event, the presence of a halogen as a substituent of the chaotropic acid, preferably fluorine or chlorine, significantly enhances the variability of chaotropicity with pH. The mechanism for this enhanced variability is unknown.

The first class of chaotropic acids includes the halogenated organic chaotropic acids. The halogenated organic chaotropic acids listed above are the preferred members of this class. As long as at least one of the halogens and a carboxylic acid group are retained, the above listed halogenated organic chaotropic acids may be modified by permutation, variation, and substitution with known equivalents.

The second class of chaotropic acid includes perchloric acid. Perchloric acid is distinguished structurally and functionally from the halogenated organic chaotropic acids. Because perchloric is a potent oxidant, it should be employed only with analytes which are resistant to oxidation or with analytes which are readily detected in their oxidized form. The concentration of perchloric acid for dissociating antibody-antigen complexes is generally lower than the corresponding concentration of halogenated organic chaotropic acid (infra).

To dissociate analyte from serum antibody and other serum components, the serum sample is combined with a chaotropic acid, viz. either a halogenated organic chaotropic acid or perchloric acid. If a halogenated organic chaotropic acid is employed, the serum should be combined with sufficient chaotropic acid to yield a solution which is 1%–20% chaotropic acid. Since the resultant mixture should have a pH of approximately 2.5 or less, sufficient chaotropic acid should be added to yield the desired pH. On the other hand, the addition of excessive chaotropic acid may denature the analyte, even though the analyte is "acid stable." The preferred addition of halogenated organic chaotropic acid to serum lies in the range of 5%–10% chaotropic acid. If perchloric acid is employed, sufficient perchloric acid should be added to yield a solution which is 1%–5% perchloric acid.

Once the chaotropic acid is combined with the serum so as to lower the pH to approximately 2.5 or less, the dissociation of analyte from serum antibody and other serum components occurs very quickly, viz. within seconds or minutes. It is preferred that the serum should remain approximately at room temperature or higher during the dissociation step. The application of heat can sometimes cause a severe precipitation of sample proteins which can render the sample difficult to handle and may interfere with the subsequent immunassay. In the other hand, chilling the serum significantly below room temperature may undesirably reduce and slow the dissociation process.

After the dissociation has occurred, the serum is then neutralized. The pH is raised so as to correspond to the optimal pH for performing the subsequent immunoassay. Typically the pH will be adjusted to approximately 7.0. Preferred neutralizing agents include neutralizing buffers, e.g., 0.5–2M TRIS.

After neutralization, the serum is ready for analysis by immunoassay. One class of preferred immunoassays is the "sandwich" immunoassay, a version of which is discribed in David (supra). However, other types of immunoassays may also be employed. If the immunoassay employs an analyte specific antibody reagent which is immobilized within "reaction wells," the pretreated serum sample may be transferred from the pretreatment well to one of the reaction wells. During the incubation in the reaction well, the analyte will bind to the immobilized antibody.

After the incubation, the pretreated serum may be decanted from the well. The well is then washed and a second analyte specific antibody reagent labeled by conjugation is added to the well. The labeled antibody reagent will bind to the analyte which remains in the well, bound to the immobilized antibody. After a second incubation, the conjugated label is then detected. Preferred labels include enzymes, fluorophores, chemiluminigenic compounds, latex beads, radionuclides, enzyme cofactors, enzyme inhibitors, etc.

EXAMPLE

A sample of canine serum is obtained from a heartworm infected animal, i.e., infected with Dirofilaria immitis. The serum sample is divided into four aliquots. The first aliquot is titrated to a pH of 2.5 with trifluoroacetic acid (TCA), rendering the aliquot approximately 2% by weight TCA. After 10 seconds, the first aliquot is then neutralized with 1M TRIS. The second and third aliquots are titrated with HCl to a pH of 2.5. After a 10 second incubation, the second aliquot is neutralized with 1M TRIS. The temperature of the third alioquot is raised to 60° C. by the application of elevated heat and is then incubated at that temperature. After 5 minutes, the third aliquot is then neutralized with 1M TRIS. The fourth aliquot is untreated.

The four aliquots are then assayed using an ELISA procedure employing immobilized anti-D. immitis and an enzyme conjugate of anti-D. immitis. Anti-D. immitis is immobilized by adsorption onto the surfaces of microtiter wells. To promote the adsorption process, 200 nanograms of monoclonal anti-D. immitis (SYNBIOTICS, Inc., San Diego, Calif. in 200 microliters sodium borate buffer is dispensed into each well of the 96 well microtiter polystyrene plate (e.g., Dynatek (TM)). The buffered antibody solution is then incubated therein for an initial four hour period at 37° C. and an additional period of 14 hour at 4° C. After the incubations, the buffered antibody solution is decanted, leaving behind adsorbed antibody. The wells are then washed three times with phosphate buffered saline containing 0.025% tween, so that only firmly adsorbed monoclonal anti-D. immitis remains. The dried microtiter plates contain immobilized anti-D. immitis, to be employed in the ELISA procedure. The enzyme conjugate of anti-D. immitis is made with monoclonal anti-D. immitis and horseradish peroxidase, according to the method of Nakane (Nakane, P. K., and Kawaio, A. T., Histochem and Cytochem, 22 1084 (1974)).

After preparing the above reaction wells with immobilized anti-D. immitis and the above enzyme conjugated anti-D. immitis reagent, material from each of the differently pretreated aliquots is transferred to a corresponding reaction well, e.g. 150 microliters of aliquot material per reaction well. The transferred material is then incubated for 30 minutes, so as to allow analyte (D. immitis antigen) to bind to the immobilized anti-D. immitis. The transferred material is then decanted and the wells are washed three times with phosphate buffered saline. After washing, only analyte bound to the immobilized anti-D. immitis will remain in the reaction well.

The presence of bound D. immitis antigen in the reaction well is detected by the addition of the enzyme conjugate. Anti-D. immitis-HRP enzyme conjugate (200 microliters) is transferred to each reaction well and incubated for 30 minutes and then decanted. The reaction wells are then washed three times with phosphate buffered saline to remove unbound enzyme conjugate. Bound enzyme conjugate is then detected by measurement of HRP activity.

HPR activity is easily assayed using a color reaction associated with oxidation of 2,2'-azino-di-(3-ethyl benzthiazoline) sulfonic acid (ABTS). An aqueous solution of ABTS is prepared having a concentration of 2 g/80 mL. The ABTS solution is stored at 4° C. A 0.01% solution of hydrogen peroxide is prepared by dilution of 30% peroxide into water. To initiate the measurement of HRP activity, 50 microliters of ABTS and 50 microliters of hydrogen peroxide are added to each well of the coated microtiter plate. The development of color is observed over 5–30 minutes. The relative absorbance for each aliquot is proportional to the presence of detectable analyte. After development of ABTS substrate, the relative absorbances of the four aliquots are as follows:

| Sample | Relative Absorbance |
|---|---|
| 1. TCA treated | 0.287 |
| 2. HCl treated w/o heat | 0.008 |
| 3. HCl treated w heat | 0.280 |
| 4. untreated | 0.013 |

The above data indicates donor serum contained antibody or other serum components which significantly interferes with the immunoassay. The above data also shows that pretreatment with either TCA or HCl significantly reduces the interference by serum components. However, the HCl pretreatment is effective only with the application of heat. Unlike the mineral acid, the TCA pretreatment does not require the application of heat.

A kit may be constructed using the reagents of the above example. The kit would include a first labeled vial for containing the TCA; a second labeled vial for containing the neutralizing agent, viz. the 1M TRIS; the microtiter plates coated with the analyte specific antibody reagent, viz. the immobilized anti-D. immitis; and a third labeled vial which contains the labeled analyte specific antibody reagent, viz. the anti-D. immitis-HRP conjugate.

What is claimed is:

1. An improved immunoassay for assaying an analyte within a serum sample, the analyte being antigenic, acid stable, and potentially bound by serum antibody, the improved immunoassay comprising the following steps:

step (1): dissociating the analyte from the serum antibody and denaturing the serum antibody by contacting the serum sample with an activated chaotrope at acid pH without the application of elevated heat, the chaotrope being of the type which is activated at room temperature by acid pH and which is de-activated by neutral pH, then step (2): de-activating the chaotrope by neutralizing the pH of the serum sample, and then step (3): performing an immunoassay on the serum sample for assaying the dissociated analyte in the presence of the denatured serum antibody, the immunoassay being of the type which is operable in the presence of de-activated chaotrope.

2. An improved immunoassay as described in claim 1 wherein the improvement further comprises the following additional steps:

step (a): prior to said step (1), loading the serum sample into a treatment well, and step (b): after said step (2) and prior to said step (3), transferring the the serum sample from the treatment well to a reaction well.

3. An improved immunoassay as described in claim 1 wherein:

in said step (1), the chaotrope is of the type which is active at room temperature at approximately pH 2.5 for dissociating the analyte from the serum antibody and for denaturing the serum antibody without denaturing the analyte.

4. An improved immunoassay as described in claim 1 wherein:

in said step (1), the chaotropic acid is selected from the group consisting of halogenated organic chaotropic acids and perchloric acid.

5. An improved immunoassay as described in claim 4 wherein:

in said step (1), the serum sample is combined with sufficient halogenated organic chaotropic acid to yield a weight percent concentration greater than 1% and less than 20% or with sufficient perchloric acid to yield a weight percent concentration greater than 1% and less than 5%.

6. An improved immunoassay as described in claim 4 wherein:

in said step (1), the serum sample is combined with sufficient halogenated organic chaotropic acid to yield a weight percent concentration greater than 5% and less than 10% or with sufficient perchloric acid to yield a weight percent concentration greater than 1% and less than 5%.

7. An improved immunoassay as described in claim 4 wherein:

the halogenated organic chaotropic acids are selected from the group consisting of trichloroacetic acid, dichloroacetic acid, chloroacetic acid, trifloroacetic acid, and difloroacetic acid.

8. An improved immunoassay as described in claim 4 wherein:

the analyte includes acid stable antigens of Dirofilaria immitis.

9. An improved immunoassay as described in claim 4 wherein:

the analyte includes acid stable antigens of feline infectious peritonitis.

10. In an improved immunoassay kit for assaying an analyte within a serum sample, the analyte being antigenic, acid stable, and potentially bound by serum antibody, the immunoassay kit of the type which includes:

immunoassay reagents for performing an immunoassay on the serum sample for assaying the analyte, the immunoassay reagents being of the type which are operable in the presence of the de-activated chaotrope described below, wherein the improvement comprises:

a chaotropic acid at acid pH, the chaotrope being of the type which is activated at a room temperature by acid pH for dissociating the analyte from the serum antibody and for denaturing the serum antibody and which is de-activated by neutral pH, and a neutralizing agent for neutralizing the serum sample and de-activating the chaotropic acid.

11. An immunoassay kit as described in claim 10 wherein:

the chaotropic acid is selected from the group consisting of halogenated organic chaotropic acids and perchloric acid.

12. An immunoassay kit as described in claim 10 wherein:

the chaotropic acid is selected from the group consisting of trichloroacetic acid, dichloroacetic acid, chloroacetic acid, trifloroacetic acid, difloroacetic acid, and perchloric acid.

13. An immunoassay kit as described in claim 12 wherein:

the neutralizing agent includes a buffer.

14. An immunoassay kit as described in claim 13 wherein:

the analyte includes acid stable antigens of Dirofilaria immitis.

15. An immunoassay kit as described in claim 13 wherein:

the analyte includes acid stable antigens of feline infectious peritonitis antigen.

* * * * *

UNITED STATES PATENT AND TRADEMARK OFFICE
CERTIFICATE OF CORRECTION

PATENT NO. : 4,703,001
DATED : October 27, 1987
INVENTOR(S) : Morton A. Vodian, et al It is certified that error appears in the above-identified patent and that said Letters Patent is hereby corrected as shown below:

In the title, Item (54) the word "Chastropic" should read -- Chaotropic --.

Column 1, line 3, "Chastropic" should read -- Chaotropic --.

Signed and Sealed this

First Day of March, 1988

Attest:

DONALD J. QUIGG

Attesting Officer

Commissioner of Patents and Trademarks